(12) United States Patent
Smith et al.

(10) Patent No.: US 8,669,131 B1
(45) Date of Patent: Mar. 11, 2014

(54) METHODS AND MATERIALS FOR FORMING GAS SENSOR STRUCTURES

(75) Inventors: Peter Smith, Summertown (GB); Jane Blake, Wallington (GB); Leon Cavanagh, Woodford (IE); Raymond Speer, Dalkey (IE)

(73) Assignee: Silicon Laboratories Inc., Austin, TX (US)

( * ) Notice: Subject to any disclaimer, the term of this patent is extended or adjusted under 35 U.S.C. 154(b) by 103 days.

(21) Appl. No.: 13/250,831

(22) Filed: Sep. 30, 2011

(51) Int. Cl.
*G01N 27/414* (2006.01)

(52) U.S. Cl.
USPC ............ 438/49; 438/610; 438/785; 438/782; 438/783; 257/253; 257/414; 427/372.2; 427/379; 427/380; 204/431

(58) Field of Classification Search
USPC ............ 438/49, 610, 782, 783, 785; 257/253, 257/414; 427/372.2–397.8; 204/431
See application file for complete search history.

(56) References Cited

U.S. PATENT DOCUMENTS

| | | | |
|---|---|---|---|
| 4,057,823 A | 11/1977 | Burkhardt et al. | |
| 4,580,439 A | 4/1986 | Manaka | |
| 4,638,346 A | 1/1987 | Inami et al. | |
| 4,649,364 A | 3/1987 | Tanahashi et al. | |
| 4,793,181 A | 12/1988 | Djorup | |
| 4,831,381 A | 5/1989 | Hester | |
| 4,849,798 A | 7/1989 | Wantanabe | |
| 4,876,890 A | 10/1989 | Mercer et al. | |
| 4,931,851 A | 6/1990 | Sibbald et al. | |
| 5,279,855 A * | 1/1994 | Hafele et al. | 427/226 |
| 5,296,125 A | 3/1994 | Glass et al. | |
| 5,357,149 A | 10/1994 | Kimura | |
| 5,481,129 A | 1/1996 | DeJong et al. | |
| 5,605,612 A | 2/1997 | Park et al. | |
| 5,801,428 A | 9/1998 | Felde et al. | |
| 5,814,281 A | 9/1998 | Williams et al. | |
| 5,878,332 A | 3/1999 | Wang et al. | |

(Continued)

FOREIGN PATENT DOCUMENTS

| | | |
|---|---|---|
| JP | 358111747 | 7/1983 |
| JP | 63103957 | 10/1986 |

(Continued)

OTHER PUBLICATIONS

Morris et al., "Pt(II) as an Electronically Active Surface Site in the Room Temperature CO Response of Pt Modified Gas Sensitive Resistors", 2011, American Chemical Society, 105, 7272-7279.*

(Continued)

*Primary Examiner* — Kimberly Rizkallah
*Assistant Examiner* — Maria Ligai
(74) *Attorney, Agent, or Firm* — Egan, Peterman, Enders LLP.

(57) ABSTRACT

Gas sensor materials and methods are disclosed for preparing and using the same to produce gas sensor structures. Also disclosed are gas sensor structures and systems that employ these disclosed materials. A gas sense-enhancing metal such as platinum may be added to a gas sensitive metal oxide material in a manner that more highly disperses the added platinum than conventional methods so as to more effectively utilize the platinum at a lower concentration, thus achieving a more cost effective solution. An ink vehicle may also be used for deposition of a gas sensitive material (e.g. on the surface of integrated circuit) that is formulated to allow "burn-out" of ink vehicle components at relatively low temperatures as compared to conventional ink vehicles.

18 Claims, 4 Drawing Sheets

(56) References Cited

U.S. PATENT DOCUMENTS

| | | | |
|---|---|---|---|
| 5,942,372 A * | 8/1999 | West et al. | 430/281.1 |
| 6,017,775 A | 1/2000 | Igel et al. | |
| 6,051,854 A | 4/2000 | Vigna et al. | |
| 6,111,280 A | 8/2000 | Gardner et al. | |
| 6,407,449 B1 | 6/2002 | Takikawa et al. | |
| 6,417,026 B2 | 7/2002 | Gotoh et al. | |
| 6,647,782 B2 | 11/2003 | Toyoda | |
| 6,673,644 B2 | 1/2004 | Gole et al. | |
| 6,690,569 B1 | 2/2004 | Mayer et al. | |
| 6,724,612 B2 | 4/2004 | Davis et al. | |
| 6,774,613 B1 | 8/2004 | Becker et al. | |
| 7,554,134 B2 | 6/2009 | Cummins | |
| 7,622,080 B2 | 11/2009 | Enquist | |
| 7,709,828 B2 | 5/2010 | Braithwaite et al. | |
| RE41,889 E | 10/2010 | Ferrari et al. | |
| 7,888,708 B2 | 2/2011 | Yazawa et al. | |
| 7,980,116 B2 | 7/2011 | Koda et al. | |
| 8,007,167 B2 | 8/2011 | Cummins | |
| 2002/0141136 A1 | 10/2002 | Toyoda et al. | |
| 2003/0010119 A1 | 1/2003 | Toyoda | |
| 2003/0010988 A1 | 1/2003 | Franson | |
| 2004/0008471 A1 | 1/2004 | Davis et al. | |
| 2005/0097941 A1 | 5/2005 | Sandvik et al. | |
| 2005/0188764 A1 | 9/2005 | Itakura et al. | |
| 2005/0199975 A1 | 9/2005 | Matubara | |
| 2008/0061323 A1 | 3/2008 | Yazawa et al. | |
| 2009/0141767 A1 | 6/2009 | Cummins | |
| 2009/0273009 A1 | 11/2009 | Cummins | |
| 2009/0308747 A1 | 12/2009 | Cramer et al. | |
| 2009/0324449 A1 | 12/2009 | Kira | |
| 2010/0098593 A1 * | 4/2010 | Trakhtenberg et al. | 422/98 |
| 2011/0089439 A1 | 4/2011 | Cummins | |
| 2011/0089472 A1 | 4/2011 | Cummins | |
| 2011/0098937 A1 | 4/2011 | Cummins | |
| 2011/0186995 A1 | 8/2011 | Alvarado et al. | |
| 2011/0197657 A1 * | 8/2011 | Gole | 73/31.05 |
| 2011/0198732 A1 | 8/2011 | Lin et al. | |
| 2011/0210446 A1 | 9/2011 | Liao et al. | |
| 2011/0226041 A1 | 9/2011 | Cummins | |
| 2012/0113650 A1 * | 5/2012 | Inoue | 362/296.02 |

FOREIGN PATENT DOCUMENTS

| | | |
|---|---|---|
| JP | 404361149 | 12/1992 |
| WO | WO2006/090433 A1 | 8/2006 |
| WO | WO2007/097025 A1 | 8/2007 |
| WO | WO2007/099933 A1 | 9/2007 |

OTHER PUBLICATIONS

Speer et al., "Gas Sensor Having Integral Heater", U.S. Appl. No. 13/250,456, filed Sep. 30, 2011, 26 pgs.

Speer et al., "Gas Sensor Utilizing Integrated Circuit Redistribution Layer", U.S. Appl. No. 13/250,432, filed Sep. 30, 2011, 26 pgs.

Speer et al., "Integrated Gas Sensor", U.S. Appl. No. 13/250,414, filed Sep. 30, 2011, 26 pgs.

Speer et al., "Systems and Methods for Packaging Integrated Circuit Gas Sensor Systems", U.S. Appl. No. 13/250,810, filed Sep. 30, 2011, 24 pgs.

Smith et al., "Gas Sensor Materials and Methods for Preparation Thereof", U.S. Appl. No. 13/250,849, filed Sep. 30, 2011, 27 pgs.

Fis, "Fis Gas Sensor, SB-500-12, for Carbon Monoxide Detection", Mar. 2006, 2 pgs.

Lemme, Elektronik, "CMOS-Sensoren gehort die Zukunft", vol. 43, No. 24, Nov. 1994, 10 pgs.

Bousse et al., "A Process for the Combined Fabrication of Ion Sensors and CMOS Circuits", IEEE Electron Device Letters, vol. 9, No. 1, Jan. 1988, 3 pgs.

Baltes et al., "Micromachined Thermally Based CMOS Microsensors", Proceedings of the IEEE, vol. 86, No. 8, Aug. 1998, 19 pgs.

Baltes et al., "The Electronic Nose in Lilliput", Proceedings of the IEEE, vol. 35, No. 9, Sep. 1998, 4 pgs.

McCartney et al., "A Fully Integrated Sensor Interface Chip", Solid State Circuits Conference Esscirc, 1999, 4 pgs.

Cratlon, "C701 802.15.4 Zigbee Ready Wireless Sensor Module", 2004, 1 pg.

Aqili et al., "Effect of Antimony Doping on the Structure, Electrical and Optical Properties of Tin Oxide Thin Films", Sci. Int, 18(1), 2006, 3 pgs.

Smith et al., "Gas Sensor Materials and Methods for Preparation Thereof", U.S. Appl. No. 13/250,849, filed Sep. 30, 2011, Office Action, Mailed May 31, 2013, 12 pgs.

Smith et al., "Gas Sensor Materials and Methods for Preparation Thereof", U.S. Appl. No. 13/250,849, filed Sep. 30, 2011, Response, Mailed Sep. 3, 2013, 12 pgs.

* cited by examiner

METHODS AND MATERIALS FOR FORMING GAS SENSOR STRUCTURES

RELATED APPLICATIONS

This application is related to the following applications, all concurrently filed on the same date as the present application, including U.S. patent application Ser. No. 13/250,414, entitled "Integrated Gas Sensor"; U.S. patent application Ser. No. 13/250,432, entitled "Gas Sensor Utilizing Integrated Circuit Redistribution Layer"; U.S. patent application Ser. No. 13/250,456, entitled "Gas Sensor Having Integral Heater"; U.S. patent application Ser. No. 13/250,810, entitled "Systems and Methods for Packaging Integrated Circuit Gas Sensor Systems"; and U.S. patent application Ser. No. 13/250,849, entitled "Gas Sensor Materials and Methods for Preparation Thereof" the disclosures of which are all expressly incorporated by reference herein in their entirety.

TECHNICAL FIELD OF THE INVENTION

The disclosure herein relates to gas sensing, and more particularly to materials for gas sensor systems.

BACKGROUND

A wide variety of gas sensor types are utilized to detect gases and other ambient air conditions. For example, electrochemical sensors are well known. Such sensors may include the use of a metal or plastic can, which houses a liquid electrolyte having electrodes immersed in the liquid. An opening or gas diffusion barrier allows atmosphere to ingress and make contact with a gas-sensing electrode. Infrared sensors are also well known. Infrared sensors advantageously utilize the characteristics of gases which show differing absorption spectrum at various infrared frequencies. Further, metal oxide based gas sensors, such as sensors employing precious metal (Pt, Pd, Au, Ag)-activated $SnO_2$, are also known. Such sensors may utilize porous metal oxides which exhibit a shift in electrical parameters when exposed to differing gases. For example, such electrical parameters may include resistance and capacitance characteristics. Such metal oxide sensors may be housed in a metal and/or plastic cylindrical can or ceramic housing with an opening provided on one end of the can to allow ingress of gas through an active charcoal filter to contact a porous metal oxide bead that is positioned within the can. Often such metal oxide based sensors utilize high operation temperatures, for example as high as 300 to 500 degrees Celsius.

It is known to add $Sb_2O_3$ to a gas sensitive $SnO_2$ material to lower resistivity to manageable values at room temperature, and to dope the material with platinum (or palladium, gold or silver) to enhance gas response kinetics and possible sensitivity. It is also known to use thick film air-fireable inks in the electronics industry to make capacitors, resistors, dielectrics and conductors. Thick film air-fireable inks have also been used to make gas sensors from platinised Sb-doped $SnO_2$ materials. Such inks typically include an ink vehicle that itself includes a volatile solvent based on terpineol or butyl carbitol and an ethyl cellulose binder. The purpose of the solvent is to both dissolve the binder and to provide a workable liquid-like form for depositing the oxide material. In conventional methods, the ink vehicle is combined with a base oxide material that has been previously prepared by combining $Sb_2O_3$ with $SnO_2$, followed by ball milling, calcining and sieving. Before combination with the ink vehicle, platinum is typically added to the previously prepared base oxide material by droplet deposition in which drops of a liquid solution of a platinum salt are applied to the surface of the base oxide material. During heating after deposition of the ink vehicle/oxide combination, the solvent evaporates at approximately 150° C., leaving behind the binder which acts like a cement in holding the powdered oxide together in a so-called "green state" and providing adhesion to the substrate. The ethyl cellulose binder requires a burn-out temperature of approximately 450° C. during later heating, at which time the metal oxide particles also start fusing together to form a sintered material that is considered to be in the "fired state". During the burn-out process, the platinum salt decomposes and particles of metallic platinum form on the metal oxide surface.

Thick film inks such as described above are typically deposited either by stencil or by screen printing. The former utilizes a solid metal screen with apertures or holes laser-drilled into it, through which the viscous ink is forced. The ink is deposited typically in one pass, with the screen thickness governing the overall wet print thickness. Screen printing is performed by forcing ink through a metal or plastic mesh with the print pattern required achieved by a combination of closed or open apertures. Screen printing allows more flexibility on printed patterns, but requires multiple prints if thicknesses greater than 20 microns are required. Also, the ink is formulated to deliver a lower viscosity than is the case with stencil inks which are more commonly referred to a 'pastes'.

Droplet deposition and spin coating are alternative deposition techniques for thick film inks. The former requires very low viscosity probably using a water-based solvent or a sol-gel formulation. Problems with clogging of the dispensing nozzle and settling of the heavy oxide particles leading to sedimentation are reported drawbacks of this technique. If very thin coatings are required (5-10 microns), spin-coating is an option, requiring the use of a photo-sensitive binder to enable patterning of the deposit through a mask. This is then followed by washing away the material not hardened by light exposure.

The use of metal oxide based gas sensor materials in combination with integrated circuit technology to provide an integrated gas sensor has been described in U.S. Pat. Nos. 7,554,134, issued Jun. 30, 2009 to Cummins, and 8,007,167, issued Aug. 30, 2011 to Cummins, both of which are assigned to the present assignee and the disclosures of both of which are expressly incorporated by reference herein in their entirety. As described in U.S. Pat. Nos. 7,554,134 and 8,007,167 a single chip wireless gas sensor may include metal oxide sensing materials combined with a microcontroller, wireless transmit/receive circuitry, and other electrical circuits, all on a single integrated circuit.

SUMMARY OF THE INVENTION

Disclosed herein are gas sensor materials (e.g., gas sensitivity enhanced gas sensitive metal oxide materials such as platinised Sb-doped $SnO_2$) and methods for preparing and using the same to produce gas sensor structures. Also disclosed are gas sensor structures and systems that employ these disclosed materials. In one embodiment of the practice of the disclosed materials and methods, a precious metal or other suitable gas sense-enhancing metal may be added to a gas sensitive metal oxide material in a manner that more highly disperses the added metal than conventional methods so as to more efficiently utilize lower concentrations of gas sense-enhancing metal, thus achieving a more cost effective solution. The resulting gas sense-enhanced metal oxide material may be employed in one exemplary embodiment to form gas sensor structures suitable for sensing the presence and/or concentration of carbon monoxide, methane, hydrogen or other VOC (volatile organic compounds) gases in a given gas mixture. The gas-sensitive metal oxide material may be a single phase n-type metal oxide such as SnO2, ZnO, $WO_3$, $TiO_2$, $In_2O_3$, $Ga_2O_3$ either used in pure form or doped with oxides such as $Sb_2O_3$ to moderate the electrical resistivity, while the gas sense-enhancing metal may be a catalyst or precious metal such as Pt, Pd, Au, Ag, or other gas sense-enhancing metal such as Cu or Ir. Such a gas sense-enhancing metal will be understood to be any metal that is suitable for increasing the sensitivity of a gas-sensitive metal oxide to one or more target gases and/or for catalyzing or facilitating gas sensing reaction kinetics (e.g., such as adsorption-desorption kinetics) to increase gas sensor speed and/or recovery.

In another exemplary embodiment, the disclosed methodology and sensor materials may be employed to form a gas sensor as part of an integrated circuit that is configured to sense the presence and/or concentration of a target gas (e.g., such as carbon monoxide and/or methane) that may be present in the ambient gaseous environment surrounding the IC gas sensor system or a package that contains the IC sensor gas system.

In another exemplary embodiment, an ink vehicle (i.e., an organic solvent and binder which may be added to the oxide to make the ink) for deposition of gas sensitive material may be formulated that allows "burn-out" to remove the ink vehicle components at relatively low temperatures (e.g., at less than or equal to about 400° C., alternatively at less than or equal to about 375° C., alternatively at less than or equal about 350° C., and further alternatively from about 300° C. to about 350° C.) as compared to conventional ink vehicles which require burn-out temperatures of at least about 450° C. In one embodiment, such an ink vehicle may be a thick film air-fireable ink, and may be applied using any suitable process (e.g., by screen printing or stencil process) to an integrated circuit to produce a gas sensor structure. Among other things, such a relatively low burn-out temperature allows one or more gas structures to be formed on an integrated circuit, at temperatures compatible with IC processing, thus allowing an integrated gas sensor system to be formed without damaging the integrated circuit. Moreover, in those exemplary embodiments where platinised metal oxide is used as the gas sensitive material, by using relatively low processing temperatures (e.g., such as about 350° C. or less) after addition of the platinum (e.g., as a platinum salt), the added platinum particles will be given reduced opportunity to grow (e.g., after decomposition of the platinum salt which occurs at about 300° C.) as compared to conventional higher temperature methods. In this regard, it is believed that higher temperatures tend to cause the resulting platinum particles in the finished gas sensor structure to be coarser, thus limiting the benefit of further addition of platinum until a crossover point is reached where the platinum particles actually interfere with carbon monoxide response of a gas sensor rather than facilitating the response.

In one respect, disclosed herein is a method for forming a gas sensor structure that includes forming a gas sensitive material formulation for deposition on a surface by combining the following components: a gas sensitive particulate material that exhibits a shift in one or more electrical parameters upon exposure to at least one target gas, a binder material having a burn-out temperature of less than or equal to about 400° C., and a solvent effective for dissolving the binder, the solvent having an evaporation temperature that is less than the burn-out temperature of the binder material. The gas sensitive particulate material, binder, and solvent may be combined at a temperature below the burn-out temperature of the binder and at a temperature below the boiling point of the solvent. The method may further include depositing the gas sensitive material formulation on the surface; exposing the deposited gas sensitive material formulation to a first temperature above the boiling point of the solvent to substantially evaporate the solvent from the deposited gas sensitive material formulation; and exposing the deposited gas sensitive material formulation to a second temperature less than or equal to about 400° C. to substantially burn-out the binder and form the gas sensor structure from the remaining gas sensitive material.

In another respect, disclosed herein is an integrated circuit including a redistribution layer (RDL) structure having a heat sensitive insulative layer present on an upper surface thereof; and a gas sensitive material formed from a deposited gas sensitive material formulation in contact with the insulative layer of the RDL structure using a binder burn-out temperature of less than or equal to about 400° C., the gas sensitive material exhibiting a shift in one or more electrical parameters upon exposure to at least one target gas, and the gas sensitive material formulation including a binder prior to being exposed to the binder burn-out temperature.

DETAILED DESCRIPTION OF THE INVENTION

Unless otherwise noted, percentage by weight values used herein represent the percentage of a given component of a mixture or solution expressed as a percentage by weight of the resulting mixture or solution that includes the given component.

Figure 1:
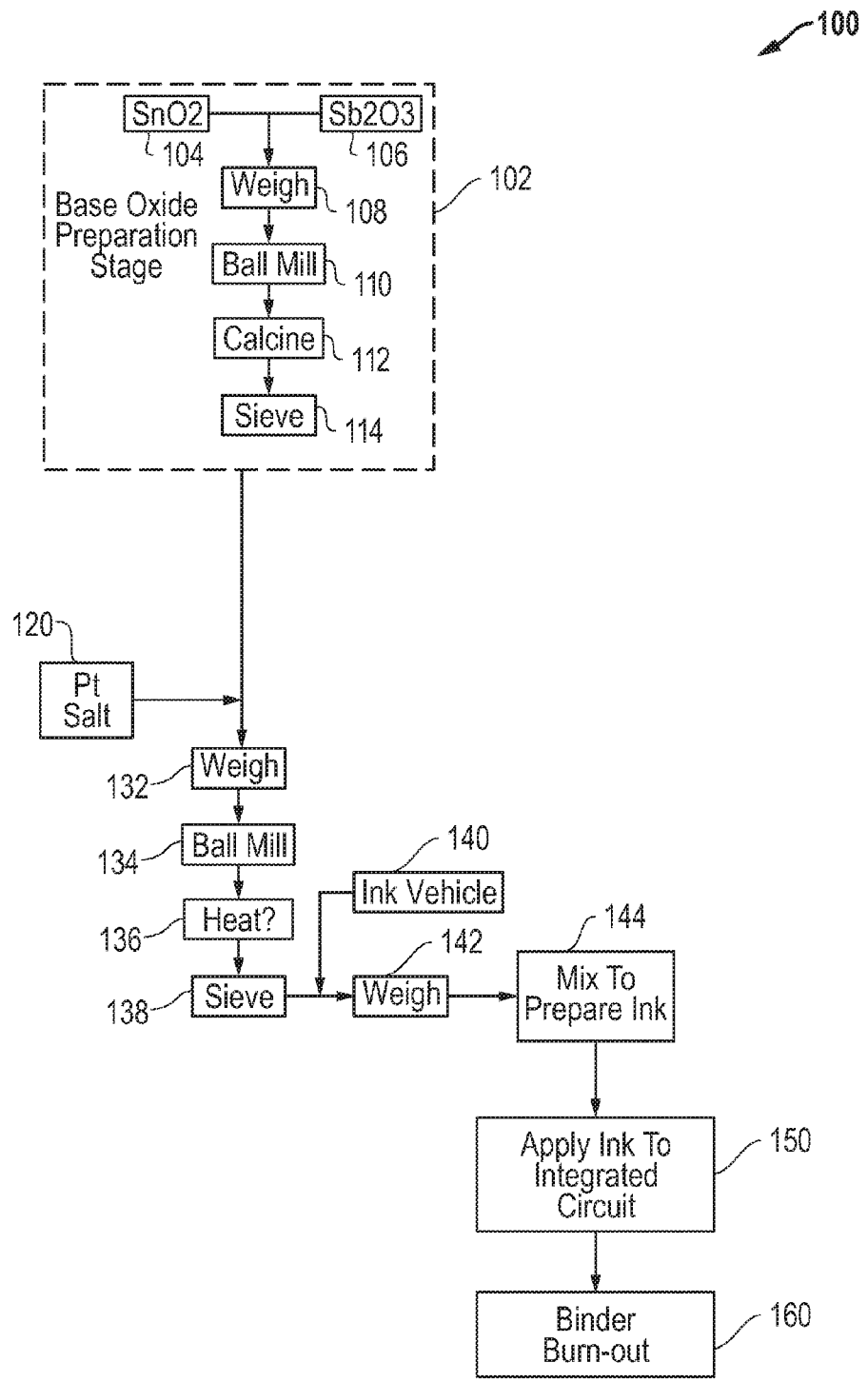
FIG. 1 illustrates a simplified process flow chart according to one exemplary embodiment of the disclosed systems and methods.

FIG. 1 illustrates a process flow chart 100 of one exemplary embodiment for preparation and application of an ink that contains a platinised gas sensitive metal oxide to any suitable substrate surface to form a gas sensor structure. Such a gas sensitive material may be a porous metal oxide which exhibits a shift in one or more electrical parameters (e.g., resistance and/or capacitance) when exposed to differing gases. As will be further described herein, in one example the ink may be applied to the surface of an integrated circuit (IC) to form the gas sensor structure thereon. As shown in FIG. 1, a base oxide preparation stage step 102 may include first combining a dopant source 106 (e.g., such as an antimony source) with a metal oxide 104. Examples of suitable metal oxides 104 include, but are not limited to, tin dioxide ($SnO_2$) or other metal oxide such as ZnO, $WO_3$, $TiO_2$, $In_2O_3$, $Ga_2O_3$ Examples of suitable dopant sources 106 include, but are not limited to, antimony oxides such as antimony trioxide ($Sb_2O_3$) or $Sb_2O_5$, or other types of dopant oxides such as $Bi_2O_3$ or $CeO_2$. It will be understood that combinations of multiple different metal oxides and/or multiple different dopant oxide sources may also be employed. In one embodiment, from about 0.1 weight % to about 2 weight % $Sb_2O_3$ (available from Sigma Aldrich, 99.99% pure) may be blended with $SnO_2$ (available from Sigma Aldrich, 99.9% pure, 325 mesh). It will be understood that greater or lesser amounts of a dopant source may be employed, and that the type and exact amount of dopant source blended with a metal oxide $SnO_2$ may be selected in one embodiment to achieve the desired resistivity of the assembled sensing layer.

As shown in FIG. 1, the combined metal oxide 104 and dopant source 106 is then weighed in step 108 for purposes of ensuring accurate control of the preparation process, although it will be understood that the metal oxide and dopant source components may be separately weighed prior to their combination. After weighing, the metal oxide and dopant source combination is then ground to provide a compositionally homogenous particulate such as a powder (e.g., to a dried agglomerated powder having a mesh size of about 75 microns) and then calcined in step 112, e.g. to a temperature of about 1100° C. for about two hours. Next, the calcined material is sieved in step 114 to obtain a metal oxide and dopant source base oxide combination that has the property of a reduced resistivity at room temperature. In this regard, resistivity of the resulting composition may be reduced in one exemplary embodiment by a factor of about 2 to about 15 times, depending on the particular selected amount of dopant source (such as $Sb_2O_3$) that is combined with the selected metal oxide (e.g., such as $SnO_2$).

Still referring to FIG. 1, a platinum salt 120 (e.g., such as tetra-amine platinum hydroxide hydrate dissolved in water or other suitable platinum source) is added in a dispersed state to the base oxide obtained from step 102 and the resulting combination is weighed in step 132 for purposes of accurate process control. For illustration purposes and as a specific example of a possible exemplary embodiment, a 1.3 wt % of tetra-amine platinum hydroxide hydrate salt may be added to a calcined mixture of 0.5 wt % $Sb_2O_3$—$SnO_2$, it being understood that this exemplary only, and that other types and relative amounts of gas sense-enhancing metal salt may be combined with a base oxide to achieve a desired loading of gas sense-enhancing metal. It will be understood that a source of a given gas sense-enhancing metal (e.g., such as Pt, Pd, Au, Ag, Cu, Ir) may be any salt of that given metal (or other material containing the given metal) that is suitable for decomposing to the corresponding gas sense-enhancing metal upon later heating, as will be described further in relation to optional step 136 and/or step 160. Next, in step 134 the combined platinum/oxide/antimony-containing combination is further ground or otherwise pulverized (e.g., by ball milling to provide a compositionally uniform mixture which is then dried and sieved through a mesh size of about 75 microns to provide agglomerated particulate material or powder having particles no longer than 75 microns).

Following step 134, may be optional heating in step 136 to a temperature and for a time suitable for decomposing the platinum salt to platinum (e.g. to a temperature of about 300° C. for about 2 hours), in this exemplary embodiment for purposes of decomposing the platinum salt to platinum at this stage, rather than the alternative embodiment of decomposing the platinum salt to platinum during the later binder burn-out step 160 (which is alternately possible). Next, the resulting highly homogeneous metal oxide material (e.g., platinised Sb-doped $SnO_2$) is passed through a sieve in step 138 for purposes of standardising the size of the platinised Sb-doped $SnO_2$ agglomerates. The sieved platinised metal oxide material may then be combined with an ink vehicle 140 that includes a solvent and a binder such as described elsewhere herein, and then weighed in step 142 for purposes of ensuring accurate process control. This solution may then be mixed in step 144 (either by ball-milling or by triple-roll milling) to prepare a well dispersed gas sensor material ink.

In one exemplary embodiment, step 134 may be alternately performed to pulverized the combined platinum/oxide/antimony-containing combination to nanoparticulate size (e.g., having a size range of about 1 nanometer to about 100 nanometers). In such an embodiment, viscosity and nature of ink vehicle 140 may be altered (e.g., including use of water-based solvent where applicable or desirable) to form a suitable viscosity gas sensitive material formulation including dispersed nanoparticulate sized gas sense-enhanced metal oxide material particles for deposition on a surface using a method such as droplet deposition, ink jet deposition, spin-on coating deposition, sol gel, etc.

Next, in step 150 the gas sensor material ink may be applied to an integrated circuit (e.g., by screen printing, stencil, or other suitable methodology) as will be further described. It will be understood that in other embodiments, a gas sensor material ink may alternatively be applied to surfaces other than an integrated circuit, e.g., such as an electrode-patterned ceramic substrate or a $SiC/SiO_2$ membrane of an electrode-patterned microhotplate, for purposes of forming a gas sensor structure. Finally, in step 160, the applied gas material ink may be heated to a first elevated temperature to evaporate the solvent to leave the metal oxide/platinum salt material and the binder in the "green state", and then to a second higher temperature to burn-out the binder material from the applied ink composition leaving the deposited metal oxide in the form of a gas sensor structure. In this regard, binder burn-out is accomplished by exposing a deposited gas-sensitive material formulation (e.g., applied ink composition) to a burn-out temperature that is sufficient to substantially remove the binder from the gas-sensitive material formulation, e.g., by combustion.

In this regard, heating to the first and second temperatures may be step-wise preformed as two separate steps, or alternately may be performed as a single heating step that continuously increases the temperature to first evaporate the solvent and then to burn-out the binder. Heating in step 160 to the second elevated temperature may also be performed for a sufficient time and to a sufficient temperature level to develop further the contacts between the oxide agglomerates themselves and between the oxide agglomerates and the metal electrodes, the material now existing in the finished "fired state." In one exemplary embodiment, the firing temperature and firing time for a platinised gas sensitive metal oxide such as platinised Sb-doped $SnO_2$ may be about 350° C. (alternately about 330° C.) for about 120 minutes, it being understood that other temperatures and times may be selected to fit each given application. However, lower temperatures may be employed where capillary forces may be sufficient to hold the deposited gas sensitive material together for a given application, and/or where nanoparticulate gas sensitive materials are employed as further described herein. It will also be understood that where optional heating step 136 is omitted, decomposition of the platinum salt to platinum may occur during the heating of step 160.

Advantageously, the mill addition of platinum salt 120 that is completed in step 134 of FIG. 1 results in a platinised metal oxide that contains platinum particles that are dispersed to a greater extent (by the higher energy impact processes of ball milling) than achieved with conventional methodology in which a platinum salt is added at the ink preparation stage where dispersion is restricted by the relatively high viscosity of the ink system, or added to the fired metal oxide coating relying on liquid impregnation of the structure by droplets dispensed from a fine bore nozzle. The methodology of this embodiment may be implemented so as to allow a smaller amount of platinum salt to be employed than conventional methodology, while achieving the same or greater gas sensitivity in a gas sensor structure formed therefrom. However, it will be understood that any other amount (weight %) of platinum may be employed, and/or that any other alternative methodology may be employed that is suitable for forming a platinised metal salt for combination with the disclosed ink vehicle compositions to form a gas sensor material ink.

Figure 2:
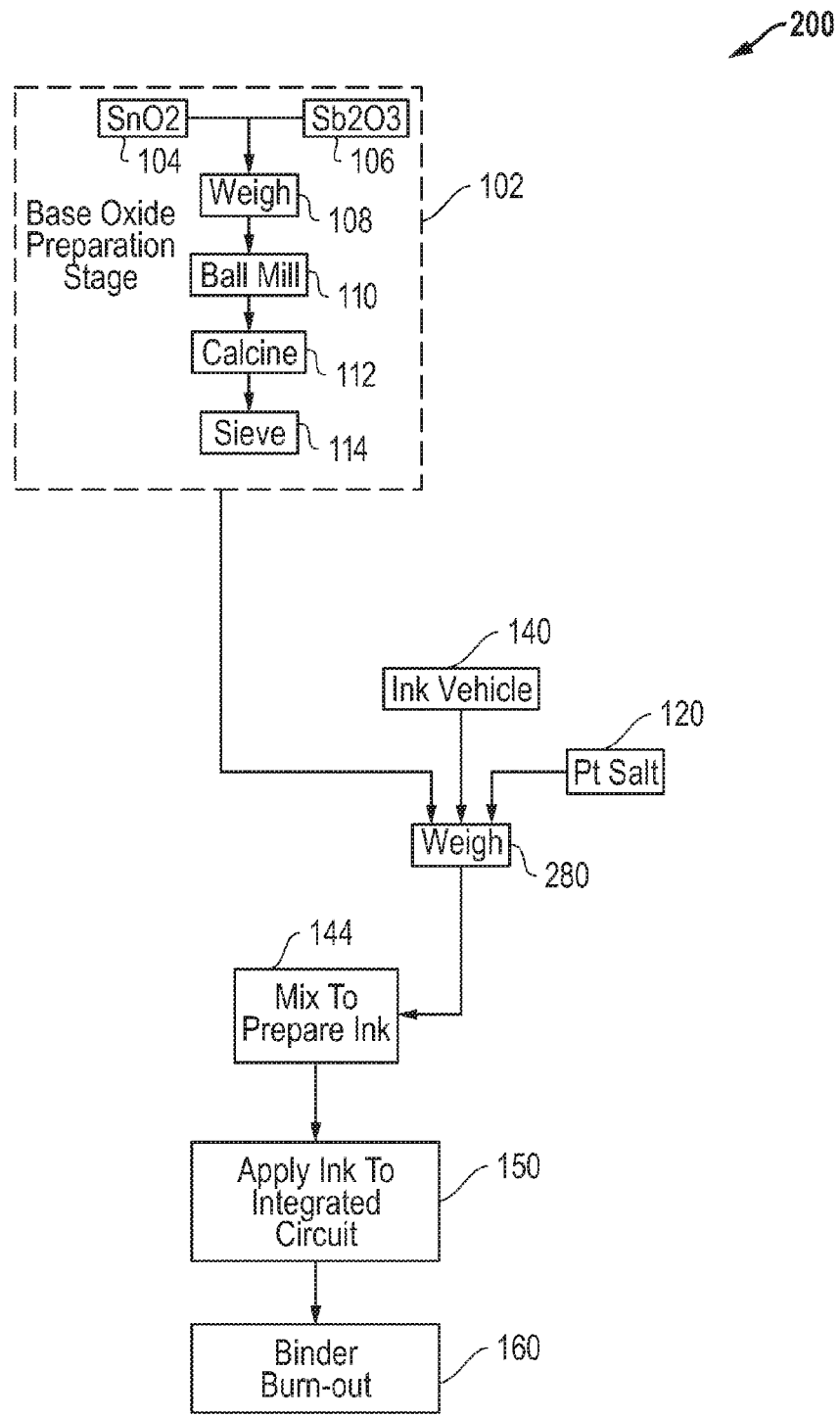
FIG. 2 illustrates a simplified process flow chart according to one exemplary embodiment of the disclosed systems and methods.

For example, FIG. 2 illustrates an alternate embodiment in which a base metal oxide is prepared using the same base oxide preparation stage step 102 as described for the embodiment of FIG. 1. However, in this alternate embodiment, a platinum salt 120 is added at the ink preparation stage from a liquid solution. The platinum liquid solution 120, the base metal oxide 102 and the ink vehicle (140) may each be individually weighed in step 280 for purpose of ensuring accurate process control, prior to mixing in step 144. However, these components may also be combined and weighed together if desired. Alternatively, the addition of platinum material in this embodiment may be accomplished, for example, by adding droplets of a liquid platinum salt 120 to the particles of the base oxide prepared in step 102, prior to combining with the ink vehicle 140. In step 150 the gas sensor material ink may be applied to an integrated circuit in similar manner, and burn out step 160 performed with optional metal oxide firing as described for the embodiment of FIG. 1.

As is known to those skilled in the art, platinum addition to $SnO_2$ increases the resistivity of the material, the magnitude of the increase varying in accordance with the level of platinum added. Therefore a convenient measure of the effectiveness of platinum dispersion is the resistivity of the platinised $SnO_2$ deposit, i.e., for a given platinum loading, the deposit with the superior dispersion should exhibit the higher resistivity. Accordingly, we have found that for a fired ink with a platinum loading of about 0.65 weight %, and made in accordance with the process described in FIG. 1, the measured resistance is about 10 times higher than for a fired ink with an even higher platinum loading of 0.7 weight % made in accordance with the process described in FIG. 2. However, it will be understood any loading of gas sense-enhancing metal on a gas-sensitive metal oxide may be employed. For example in one exemplary embodiment, gas sense-enhancing metal loading may be from about 0.1 wt % to about 2 wt %, although greater and lesser loading amounts are also possible.

In addition to the above described methodology and materials, also disclosed herein are ink vehicle compositions that include solvent and binder components that are heat removable from the ink vehicle composition at temperatures that are less than or equal to about 400° C., alternatively less than about 350° C., and further alternatively at temperatures from about 300° C. to about 350° C. Such temperatures are lower than conventional ink vehicle burn-out temperatures, and are sufficiently low to be compatible with the CMOS processed/post-processed materials of underlying or associated components of a gas sensor structure or system. Thus gas sensor structures may be formed using a gas sensitive material ink that is composed of the disclosed ink vehicle compositions together with a metal oxide gas sensitive material (e.g., such as platinised Sb-doped $SnO_2$), or other type of gas sensitive material.

In one exemplary embodiment disclosed herein, an ink vehicle composition may include a binder mixed together with an organic vehicle or solvent that is suitable for dissolving the particular selected binder, and for providing a workable liquid-like form suitable for depositing a metal oxide that is mixed therewith to form a thick film air-fireable ink that includes the metal oxide material. Examples of types of suitable solvents include, but are not limited to, alcohols, ethers, mineral spirits, pine oils, etc. and combinations thereof. Specific examples of suitable solvents include, but are not limited to, terpineol, diethylene gylcol butyl ether, etc. and combinations thereof. It will be understood that a particular solvent type may be selected based on desired evaporation temperature (the boiling point temperature of the solvent or the temperature at which the solvent evaporates from the composition at desired time and temperature) for a given application and based on the ability of the selected solvent to solubilize the corresponding binder material present in the same ink vehicle composition to a state (e.g., liquid, viscous liquid, paste, etc.) that is suitable for facilitating deposition of a gas sensitive metal oxide in an ink formed therefrom. In one embodiment, the boiling point of the selected solvent is less than the burn-out temperature of the selected binder. The amount of the selected solvent within the overall ink vehicle composition may vary, but in one embodiment the solvent amount may range from about 80% to about 97% by weight of the prepared ink vehicle, it being understood that amounts greater or lesser than this range are also possible.

A binder material for use with a solvent in an ink vehicle composition may be any material selected to act as a cement or to otherwise hold together a powdered metal oxide in a "green state" following evaporation of the solvent from the composition at a temperature which is lower than the burn-out temperature of the binder. The selected binder within the overall ink vehicle composition may be present in an amount to achieve a desired viscosity of the ink vehicle composition or the final gas sensitive ink material to fit a given application. In one exemplary embodiment, the selected binder may be present in an amount, for example, that ranges from about 88% to about 98% by weight of the prepared ink vehicle, and the binder may represent the balance of the ink vehicle composition other than the solvent. However, it will be understood that the amount of binder may be greater or lesser than the above binder compositional range, and/or that other materials may be optionally present in the prepared ink vehicle besides solvent and binder.

A binder material may be further selected in one exemplary embodiment to burn out at a temperature of about 400° C. or less. Examples of types of binder materials having such a burn out temperature range include but, are not limited to C1 to C6 alkyl acrylate or C1 to C6 alkyl methacrylate polymers. Specific examples of such binder materials include, but are not limited to, polymers such as poly (iso-propyl acrylate), poly (iso-butyl acrylate), poly (iso-pentyl acrylate), poly (iso-propyl methacrylate), poly (iso-butyl methacrylate), poly (iso-pentyl methacrylate), etc. and combinations thereof. It will be understood that a particular binder material may be selected based on desired burn-out (e.g., sublimation, decomposition) temperature for a given application, the ability to support a 'clean' burn-out (i.e., no residues or burn-out products that contaminate the sensor surface), the ability to support an ink system of suitable viscosity characteristics for printing, and based on the ability of the binder material to hold together the powdered metal oxide in the green state.

Figure 3:
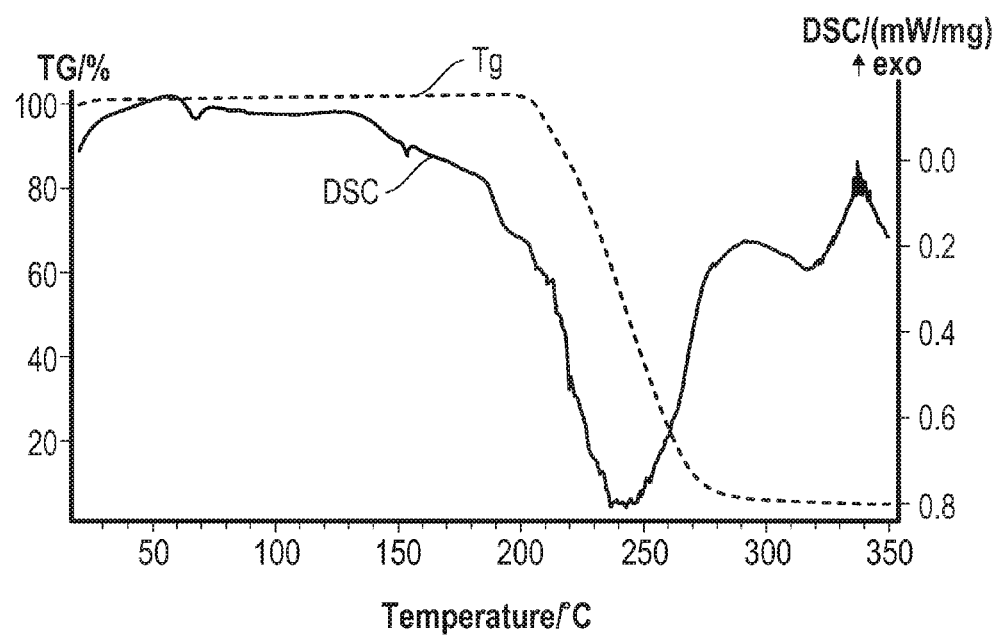
FIG. 3 illustrates a plot of differential scanning calorimetry (DSC) and glass transition temperature (Tg) for a polyacrylate binder material according to one exemplary embodiment of the disclosed systems and methods.
Figure 4:
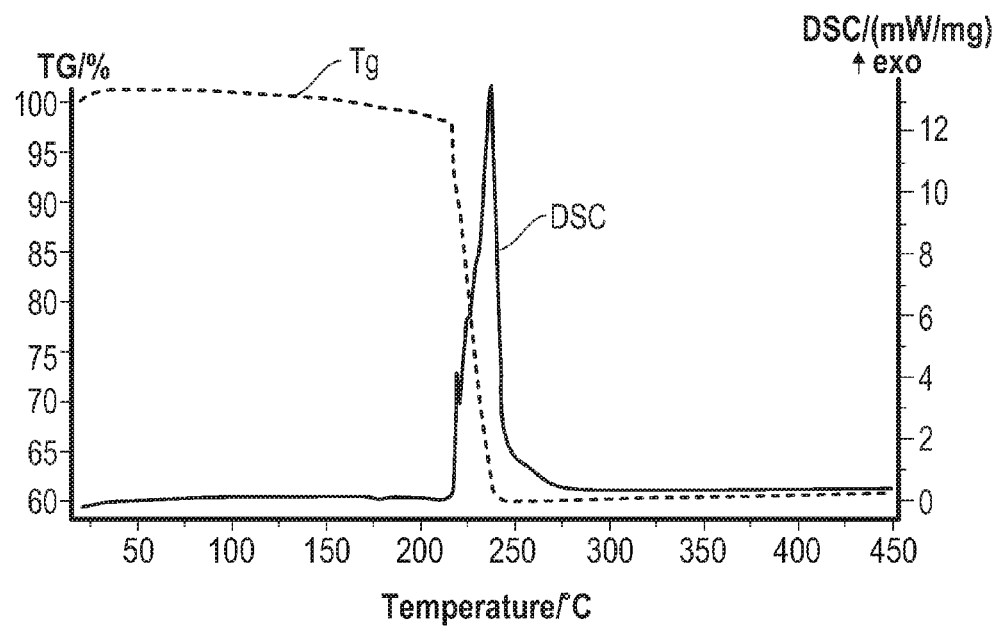
FIG. 4 illustrates a plot of differential scanning calorimetry (DSC) and glass transition temperature (Tg) for decomposition of a platinum salt to platinum according to one exemplary embodiment of the disclosed systems and methods.

FIG. 3 illustrates a plot of differential scanning calorimetry (DSC) and glass transition temperature (Tg) for a poly (iso-butyl methacrylate) binder material at increasing temperature. As may be seen in FIG. 3, sublimation of this binder material occurs over the range of approximately 230° C. to about 290° C. FIG. 4 illustrates a plot of differential scanning calorimetry (DSC) and glass transition temperature (Tg) for decomposition of a tetra-amine Platinum (II) hydroxide hydrate salt to elemental platinum at increasing temperature. As may be seen in FIG. 4, decomposition of the platinum salt occurs over the range of approximately 220° C. to about 250° C. As may be seen, both the binder sublimation process of FIG. 3 and the platinum salt decomposition of FIG. 4 occur at temperatures below 300° C.

In one exemplary embodiment, a gas sensitive material ink that contains a platinised gas sensitive metal oxide may be prepared as follows. An ink vehicle (e.g., such as ink vehicle 140 of the embodiment of FIG. 1 or 2) may be prepared by combining an organic vehicle in the form of a terpineol solvent with about 10% polyacrylate by weight of the total combined solution. This combination may be performed at room temperature or any other suitable temperature. The prepared ink vehicle may be combined with a base oxide prepared using the methodology described in the embodiments of FIG. 1 or 2 or any other suitable methodology. For example, in one exemplary embodiment, a Sb-doped $SnO_2$ base oxide may be first prepared by combining $SnO_2$ with from about 0.1% to about 10% by weight of $Sb_2O_3$. The resulting base oxide may then be combined with from about 0.1% to about 10% by weight of platinum salt to form the gas sensitive material ink (e.g., using the methodology of FIG. 1 or 2 or other suitable methodology).

As previously described in relation to FIGS. 1 and 2, the disclosed gas sensitive material inks may be applied to an integrated circuit or other suitable substrate surface to form one or more gas sensor structures thereon. In this regard, an integrated circuit may be any type of electronic circuitry suitable for utilization with one or more sensor elements for detecting characteristics of gas compositions. It is often desirable to prevent exposure of a completed integrated circuit to temperatures above about 400° C., and the disclosed gas sensitive material inks may thus be advantageously deposited and processed to form one or more gas sensor structures on an integrated circuit without exceeding this 400° C. level.

Figure 5:
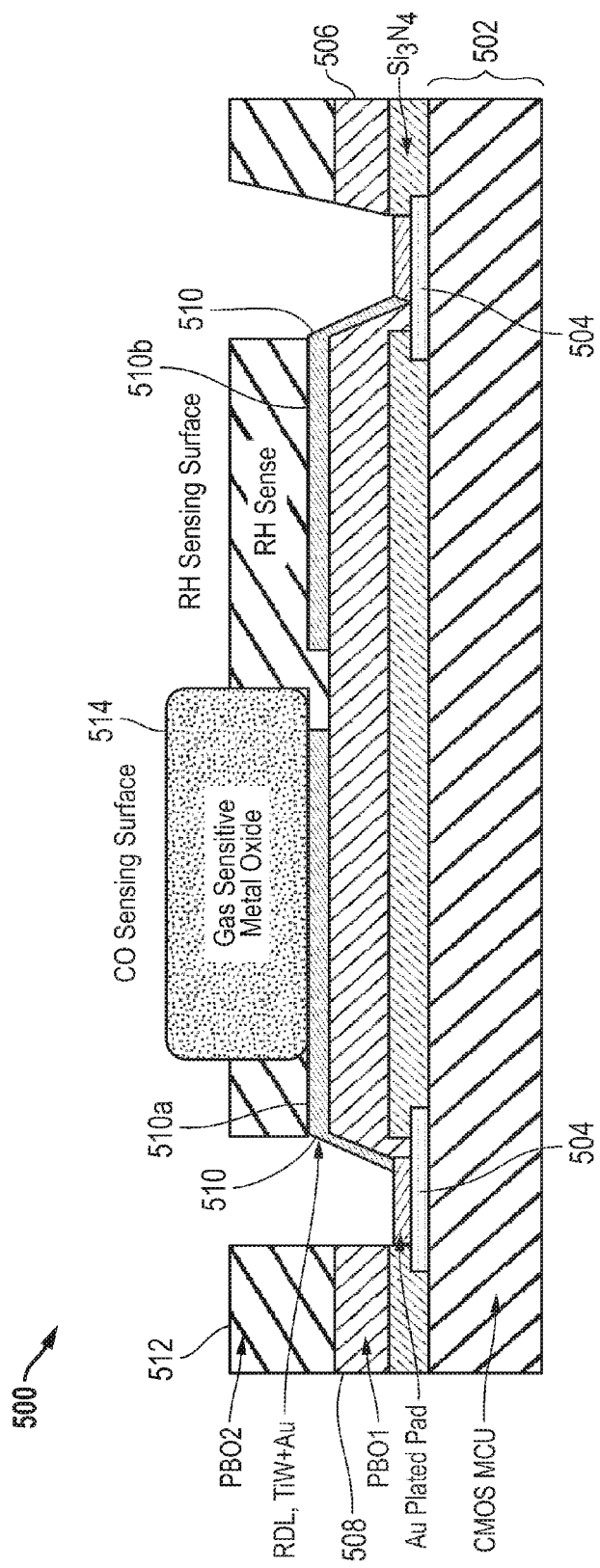
FIG. 5 illustrates an exemplary cross section of an integrated circuit according to one exemplary embodiment of the disclosed systems and methods.

FIG. 5 illustrates an exemplary cross section of an integrated circuit 500 having a gas sensor structure that includes a layer 514 of gas sensitive metal oxide that may be formed according to the disclosed methods and compositions. Integrated circuit 500 may be, for example, a mixed signal system on a chip circuit that includes a processor such as an 8051 compatible microcontroller in combination with associated memory elements as described in more detail in concurrently filed U.S. patent application Ser. No. 13/250,414, entitled "Integrated Gas Sensor", the disclosure of which is expressly incorporated herein by reference in its entirety.

As shown in FIG. 5, integrated circuit 500 includes analog and digital circuitry that may be provided as a CMOS structure 502. As further shown, bond pads 504 are provided to allow external connections to the integrated circuit (such as through bond wires or solder bumps), and a top passivation layer 506, such as for example a silicon nitride layer, may be provided to environmentally seal and protect the CMOS structure 502. An additional insulative layer 508 may be formed atop the passivation layer 506 with an additional conductive layer 510 thereon for contact with electrodes using redistribution layer (RDL) technology known in the semiconductor processing art. In this exemplary embodiment, such RDL technology may be utilized to form and pattern a gas sensor and humidity sensor, e.g., inclusive of sensing, reference and heater electrodes, above a standard integrated circuit, although alternative technology may be utilized to form and pattern a sensor atop the integrated circuit.

Insulative layer 508 may be any of a wide range of insulating materials, often polymer base and in one exemplary non-limiting example, a polybenzoxazole (PBO) layer and alternatively a polyimide layer, while conductive layer 510 (which may include portions 510a and 510b) may be formed of a wide range of conductive materials and in one exemplary non-limiting example, a titanium/tungsten/gold/titanium (TiW—Au—Ti) layer as described in more detail in said concurrently filed U.S. patent application Ser. No. 13/250, 414, entitled "Integrated Gas Sensor", the disclosure of which is expressly incorporated herein by reference in its entirety. As known in the art, the PBO layers may be heat cured after formation, e.g., at a temperature of about 350° C., and may be characterized as heat sensitive in the sense that they are incompatible (i.e., they deteriorate or are otherwise damaged or molecularly degraded) with higher temperatures such as the 450° C. burn-out temperatures required by conventional thick film air-fireable inks. Other insulative materials such as polyimides may also be characterized as heat sensitive and incompatible with conventional air-fireable ink temperatures. Thus, insulative layers 508 and 512 of FIG. 5 may be in one embodiment characterized as incompatible with temperatures greater or equal to 450° C., alternatively incompatible with temperatures greater than 425° C., alternatively incompatible with temperatures greater than 400° C., alternatively incompatible with temperatures greater than 375° C., and alternatively incompatible with temperatures greater than 350° C.

Still referring to FIG. 5, gas sensitive layer 514 may be, in a non-limiting example, a gas sensitive metal oxide layer (e.g., of about 30 microns in thickness) that is deposited using the materials and methods described herein, and/or may be any other of a wide range of gas sensitive materials that may be deposited using the disclosed low temperature burn-out ink compositions. In this regard, the gas sensitive materials utilized may also depend upon the desired gas(es) to be detected. For example, in one non-limiting embodiment, carbon monoxide (CO) or hydrogen may be detected, and the gas sensitive material may be a tin oxide ($SnO_2$) doped with platinum and antimony as described elsewhere herein. As shown in FIG. 5, portions 510a of the RDL conductor and gas sensitive material 514 may be utilized in one exemplary embodiment for sensing a gas through exposure of the gas sensitive material to a gas containing atmosphere. Similarly, conductor portions 510b and the second PBO layer 512 may be utilized in one exemplary embodiment for sensing humidity levels in the atmosphere.

The disclosed gas sensitive material formulations may be deposited as layer 514 on integrated circuit 500 of FIG. 5 (e.g., on top and/or adjacent to RDL layer 510 and PBO layers 508 and 512 of integrated circuit 500), or as a layer on any other suitable substrate surface using any deposition technology suitable for the specific application. For example, in one exemplary embodiment, a gas sensitive material ink may be deposited as a thick film gas sensitive material ink on an integrated circuit 500 using either a stencil or a screen printing process. A stenciling deposition embodiment may utilize, for example, a solid metal screen having a desired pattern of apertures or holes that are lasered drilled into it, and may employ a higher viscosity ink (e.g., paste) that may be deposited in one pass, with the screen thickness governing the overall wet print thickness. Such stencil processing may advantageously be used due to similarities to back-end integrated circuit packaging processes which utilize stencil deposition for solder paste deposition for flip chip packaging. A screen printing embodiment may be employed to force an ink having lower viscosity than is used for stenciling through a metal or plastic mesh with the print pattern required achieved by a combination of closed or open apertures. Screen printing may allow for more flexibility on printed patterns, but may sometimes require multiple prints or passes if thicknesses greater than about 20 microns are required.

It will be recognized that the gas sensitive layer 514 may be formed from the disclosed compositions in many other different manners and combinations thereof, including for example but not limited to, deposition processes, printing processes (including but not limited to ink-jet, screen, stencil, etc. printing), electroplating and the like. The gas sensitive material may also be deposited by spin-on coating, which covers the whole wafer surface, followed by removal of excess material for all regions except the sensor site. Spin coating may be particularly useful where relatively thin coatings are required (e.g., about 5-10 microns), and may employ a photo-sensitive binder to enable patterning of the deposited material through a mask. This is then followed by washing away the material not hardened by light exposure. Droplet deposition may also be employed with a relatively low viscosity gas sensitive material solution, e.g., formulated with a water-based solvent.

It will be understood that viscosity of a gas sensitive material formulation may be selected to fit the particular deposition methodology employed, e.g., liquid, viscous liquid, paste, etc. Exemplary viscosity ranges for a few possible deposition methods are listed below in Table 1 as measured at low shear ($10^{-5}$-$10^{-4}$ s$^{-1}$). It will be understood that these values are exemplary only, and that gas sensitive material formulations have greater or lesser viscosities may also be employed.

TABLE 1

| Deposition Method | Viscosity at Low Shear ($10^{-5}$ – $10^{-4}$ s$^{-1}$) |
| --- | --- |
| Droplet Deposition/Spin Coating | 1 to 20 MPa*s |
| Screen Printing Inks | $10^3$ to $10^4$ MPa*s |
| Stencil Inks | $10^4$ to $10^5$ MPa*s |

The integrated circuit of FIG. 5 may be packaged in any of a wide variety of semiconductor packages and the techniques described herein are not limited to a particular type of integrated circuit package. Rather, it is only desirable that the gas sensing material and humidity sensing material formed in the RDL layers be exposed to the atmosphere that is being measured. One exemplary embodiment of a suitable package is shown in concurrently filed U.S. patent application Ser. No. 13/250,810, entitled "Systems and Methods for Packaging Integrated Circuit Gas Sensor Systems," the disclosure of which is incorporated herein by reference.

As described elsewhere herein, the disclosed methods may be practiced in one embodiment using burn-out temperatures of less than about 350° C., and/or using burn-out temperatures that are below the sintering temperature of the given deposited gas sensitive material. In such embodiments, the cohesive strength between individual gas sensitive material particles and the adhesive strength between the gas sensitive material and a substrate surface may be increased by using dispersions of nanoparticulate-sized particles (e.g., such as nanoparticles of the types of platinised gas sensitive metal oxides described elsewhere herein or specific "binding" additives such as fumed silica or synthetic clays). In one exemplary embodiment, such nanoparticulate-sized particles may be characterized as having a size range of about 1 nanometer to about 100 nanometers. Such nanoparticles may have very high surface areas that provide a powerful driving force for the individual particles to stick together, resulting in increased cohesive and adhesive strength, in a manner as may be observed for dried mud having clay platelets that provide the binding effect. Thus, additives and components of the gas sensitive material ink compositions described herein may be selected to be nanoparticulate high surface area materials that increase cohesion and adhesion characteristics of the deposited gas sensitive material, e.g., where low burn-in temperatures such as less than about 350° C. are employed.

Further modifications and alternative embodiments of this invention will be apparent to those skilled in the art in view of this description. It will be recognized, therefore, that the present invention is not limited by these example arrangements. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the implementations and architectures. For example, equivalent elements may be substituted for those illustrated and described herein and certain features of the invention may be utilized independently of the use of other features, all as would be apparent to one skilled in the art after having the benefit of this description of the invention.

The invention claimed is:

1. A method for forming a gas sensor structure, comprising forming the gas sensor structure without exceeding a temperature of about 400° C. using the following steps:
   forming a gas sensitive material formulation for deposition on a surface by combining the following components:
      a gas sensitive particulate material that exhibits a shift in one or more electrical parameters upon exposure to at least one target gas,
      a binder material having a burn-out temperature of less than or equal to about 400° C., and
      a solvent effective for dissolving the binder, the solvent having an evaporation temperature that is less than the burn-out temperature of the binder material,
      where the gas sensitive particulate material, binder, and solvent are combined at a temperature below the burn-out temperature of the binder and at a temperature below the boiling point of the solvent;
   depositing the gas sensitive material formulation on the surface;
   exposing the deposited gas sensitive material formulation to a first temperature above the boiling point of the solvent to substantially evaporate the solvent from the deposited gas sensitive material formulation; and
   exposing the deposited gas sensitive material formulation to a second temperature less than or equal to about 400° C. to substantially burn-out the binder and form the gas sensor structure from the remaining gas sensitive material.

2. The method of claim 1, further comprising forming the gas sensor structure without exceeding a temperature of about 350° C.; where the binder material has a burn-out temperature of less than about 350° C.; and where the method further comprises exposing the deposited gas sensitive material formulation to a second temperature less than or equal to about 350° C. to substantially burn-out the binder and form the gas sensor structure from the remaining gas sensitive material.

3. The method of claim 1, further comprising forming the gas sensor structure without exceeding a temperature of about 300° C.; where the binder material has a burn-out temperature of less than about 300° C.; and where the method further comprises exposing the deposited gas sensitive material formulation to a second temperature less than or equal to about 300° C. to substantially burn-out the binder and form the gas sensor structure from the remaining gas sensitive material.

4. The method of claim 1, further comprising depositing the gas sensitive material formulation on a surface of an integrated circuit; and exposing the deposited gas sensitive material formulation to the first and second temperatures without damaging the underlying integrated circuit to form the gas sensor structure as part of an integrated gas sensor system that includes the integrated gas sensor structure.

5. The method of claim 4, where the integrated circuit comprises at least one insulative layer that is incompatible with temperatures greater or equal to about 450° C.

6. The method of claim 4, further comprising forming the gas sensor structure without exceeding a temperature of about 350° C.; and where the integrated circuit comprises at least one insulative layer that is incompatible with temperatures greater or equal to about 450° C.

7. The method of claim 4, further comprising forming the gas sensor structure on the surface of the integrated circuit without exceeding a temperature of about 300° C.; and where the integrated circuit comprises at least one insulative layer that is incompatible with temperatures greater or equal to about 450° C.

8. The method of claim 1, further comprising depositing the gas sensitive material formulation on a surface of an integrated circuit in contact with at least one polyimide or polybenzoxazole (PBO) insulative layer.

9. The method of claim 1, where the step of depositing the gas sensitive material formulation on the surface comprises at least one of stencil or screen printing the gas sensitive material formulation on the surface.

10. The method of claim 1, further comprising combining the solvent and the binder to form an ink vehicle composition; and then combining the ink vehicle composition with the gas sensitive particulate material to form the gas sensitive material formulation.

11. The method of claim 10, where the step of depositing the gas sensitive material formulation on the surface comprises at least one of stencil or screen printing the gas sensitive material formulation on the surface.

12. The method of claim 1, where the binder comprises at least one of a polymer of C1 to C6 alkyl acrylate monomer, a polymer of C1 to C6 alkyl methacrylate, or a combination thereof.

13. The method of claim 1, where the binder comprises at least one of poly (iso-propyl acrylate), poly (iso-butyl acrylate), poly (iso-pentyl acrylate), poly (iso-propyl methacrylate), poly (iso-butyl methacrylate), poly (iso-pentyl methacrylate), or a combination thereof.

14. The method of claim 13, where the gas sensitive particulate material comprises platinised Sb-doped $SnO_2$.

15. The method of claim 1, where the target gas comprises at least one of carbon monoxide, methane, hydrogen, or a combination thereof.

16. The method of claim 1, where the second temperature is higher than the first temperature.

17. The method of claim 1, further comprising forming the gas sensor structure without exceeding a temperature of about 350° C.; where the gas sensitive material formulation comprises platinised metal oxide.

18. The method of claim 1, further comprising forming the gas sensor structure without exceeding a temperature of about 300° C.; where the gas sensitive material formulation comprises platinised metal oxide.

* * * * *